(12) United States Patent
Gill et al.

(10) Patent No.: US 8,231,383 B2
(45) Date of Patent: Jul. 31, 2012

(54) CURING LIGHT INSTRUMENT

(75) Inventors: Owen Gill, Southbury, CT (US); John Klinger, Sandy Hook, CT (US); Alex Lippay, Kent, CT (US)

(73) Assignee: Kerr Corporation, Orange, CA (US)

( * ) Notice: Subject to any disclaimer, the term of this patent is extended or adjusted under 35 U.S.C. 154(b) by 814 days.

(21) Appl. No.: 11/671,563

(22) Filed: Feb. 6, 2007

(65) Prior Publication Data
US 2007/0134616 A1  Jun. 14, 2007

Related U.S. Application Data

(63) Continuation of application No. 10/215,210, filed on Aug. 8, 2002, now Pat. No. 7,182,597.

(51) Int. Cl.
*A61C 3/00* (2006.01)

(52) U.S. Cl. .......................................................... 433/29

(58) Field of Classification Search .................... 433/29, 433/28, 31, 215, 229; 362/119, 800, 804, 362/327, 572–573; 606/2, 13, 16–17; 607/88; 385/115–116, 119–120
See application file for complete search history.

(56) References Cited

U.S. PATENT DOCUMENTS

| | | |
|---|---|---|
| 3,638,013 A | 1/1972 | Keller |
| 3,712,984 A | 1/1973 | Lienhard |
| 3,733,481 A | 5/1973 | Kuyt |
| 3,868,513 A | 2/1975 | Gonser |
| 3,970,856 A | 7/1976 | Mahaffey et al. |
| RE29,421 E | 9/1977 | Scott |
| 4,048,490 A | 9/1977 | Troue |
| 4,114,274 A | 9/1978 | Jones |
| 4,114,946 A | 9/1978 | Hoffmeister et al. |
| 4,149,086 A | 4/1979 | Nath |
| 4,185,891 A | 1/1980 | Kaestner |
| 4,186,748 A | 2/1980 | Schlager |
| 4,209,907 A | 7/1980 | Tsukada et al. |
| 4,221,994 A | 9/1980 | Friedman |
| 4,229,658 A | 10/1980 | Gonser |
| 4,230,453 A | 10/1980 | Reimers |

(Continued)

FOREIGN PATENT DOCUMENTS

CA  2298992  9/2000

(Continued)

OTHER PUBLICATIONS

Two-page International Search Report for EP07020186 mailed Jan. 7, 2009.

(Continued)

*Primary Examiner* — Cris L Rodriguez
*Assistant Examiner* — Hao D Mai
(74) *Attorney, Agent, or Firm* — Wood, Herron & Evans, LLP

(57) ABSTRACT

The present invention provides a handheld portable, efficient instrument for curing light-curable compounds. The instrument comprises a housing, a light emitted structure supported in the housing, and a reflector configured to interface with the light emitting structure such that light emitted is captured and directed by the reflector onto a light-curable compound. The reflector maximizes the amount of light transferred and contacting the light-curable compound thereby reducing the instrument=s power requirements and improving efficiency. The light emitting structure comprises state of the art, energy efficient, light generating dies. The curing light instrument may also have a self-contained power supply lending portability and convenient of use.

34 Claims, 4 Drawing Sheets

U.S. PATENT DOCUMENTS

| | | | |
|---|---|---|---|
| 4,233,649 A | 11/1980 | Scheer et al. | |
| 4,280,273 A | 7/1981 | Vincent | |
| 4,298,806 A | 11/1981 | Herold | |
| 4,308,120 A | 12/1981 | Pennewiss et al. | |
| 4,337,759 A | 7/1982 | Popovich et al. | |
| 4,385,344 A | 5/1983 | Gonser | |
| RE31,279 E | 6/1983 | Mefferd et al. | |
| 4,391,588 A | 7/1983 | Matsui | |
| 4,398,885 A | 8/1983 | Loge et al. | |
| 4,412,134 A | 10/1983 | Herold et al. | |
| 4,445,858 A | 5/1984 | Johnson | |
| 4,450,139 A | 5/1984 | Bussiere et al. | |
| 4,610,630 A | 9/1986 | Betush | |
| 4,666,406 A | 5/1987 | Kanca, III | |
| 4,673,353 A | 6/1987 | Nevin | |
| 4,716,296 A | 12/1987 | Bussiere et al. | |
| 4,729,076 A | 3/1988 | Masami et al. | |
| 4,757,381 A | 7/1988 | Cooper et al. | |
| 4,762,862 A | 8/1988 | Yada et al. | |
| 4,792,692 A | 12/1988 | Herold et al. | |
| 4,810,194 A | 3/1989 | Snedden | |
| 4,826,431 A | 5/1989 | Fujimura et al. | |
| 4,836,782 A | 6/1989 | Gonser | |
| 4,839,566 A | 6/1989 | Herold et al. | |
| 4,846,546 A | 7/1989 | Cuda | |
| 4,888,489 A | 12/1989 | Bryan | |
| 4,935,665 A | 6/1990 | Murata | |
| 4,936,808 A | 6/1990 | Lee | |
| 4,948,215 A | 8/1990 | Friedman | |
| 4,963,798 A | 10/1990 | McDermott | |
| 4,999,310 A | 3/1991 | Kim | |
| 5,003,434 A | 3/1991 | Gonser et al. | |
| 5,007,837 A | 4/1991 | Werly | |
| 5,017,140 A | 5/1991 | Ascher | |
| 5,029,957 A | 7/1991 | Hood | |
| 5,070,258 A | 12/1991 | Izumi et al. | |
| 5,115,761 A | 5/1992 | Hood | |
| 5,147,204 A | 9/1992 | Patten et al. | |
| 5,150,016 A | 9/1992 | Sawase et al. | |
| 5,161,879 A | 11/1992 | McDermott | |
| 5,162,696 A | 11/1992 | Goodrich | |
| 5,173,810 A | 12/1992 | Yamakawa | |
| RE34,196 E | 3/1993 | Munro | |
| 5,189,751 A | 3/1993 | Giuliani et al. | |
| 5,198,678 A | 3/1993 | Oppawsky | |
| 5,201,655 A | 4/1993 | Friedman | |
| 5,233,283 A | 8/1993 | Kennedy | |
| 5,242,602 A | 9/1993 | Richardson et al. | |
| 5,265,792 A | 11/1993 | Harrah et al. | |
| 5,278,629 A | 1/1994 | Schlager et al. | |
| 5,283,425 A | 2/1994 | Imamura | |
| 5,290,169 A | 3/1994 | Friedman et al. | |
| 5,302,124 A | 4/1994 | Lansing et al. | |
| 5,312,249 A | 5/1994 | Kennedy | |
| 5,316,473 A | 5/1994 | Hare | |
| 5,328,368 A | 7/1994 | Lansing et al. | |
| 5,371,826 A | 12/1994 | Friedman | |
| 5,373,114 A | 12/1994 | Kondo et al. | |
| 5,420,768 A | 5/1995 | Kennedy | |
| 5,457,611 A | 10/1995 | Verderber | |
| 5,471,129 A | 11/1995 | Mann | |
| 5,487,662 A | 1/1996 | Kipke et al. | |
| 5,521,392 A | 5/1996 | Kennedy et al. | |
| 5,530,632 A | 6/1996 | Shikano et al. | |
| 5,535,230 A | 7/1996 | Abe | |
| 5,616,141 A | 4/1997 | Cipolla | |
| 5,617,492 A | 4/1997 | Beach et al. | |
| 5,634,711 A | 6/1997 | Kennedy et al. | |
| 5,660,461 A | 8/1997 | Ignatius et al. | |
| 5,664,042 A | 9/1997 | Kennedy | |
| 5,678,998 A | 10/1997 | Honkura et al. | |
| 5,698,866 A | 12/1997 | Doiron et al. | |
| 5,707,139 A | 1/1998 | Haitz | |
| 5,711,665 A | 1/1998 | Adam et al. | |
| 5,741,132 A | 4/1998 | Usui et al. | |
| 5,747,363 A | 5/1998 | Wei et al. | |
| 5,759,032 A | 6/1998 | Bartel | |
| 5,803,729 A | 9/1998 | Tsimerman | |
| 5,857,767 A | 1/1999 | Hochstein | |
| 5,912,470 A | 6/1999 | Eibofner et al. | |
| 5,928,220 A | 7/1999 | Shimoji | |
| 5,931,676 A | 8/1999 | Honkura et al. | |
| 5,975,895 A | 11/1999 | Sullivan | |
| 6,008,264 A | 12/1999 | Ostler et al. | |
| 6,033,223 A | 3/2000 | Narusawa et al. | |
| 6,045,240 A | 4/2000 | Hochstein | |
| 6,046,460 A | 4/2000 | Mertins | |
| 6,065,965 A | 5/2000 | Rechmann | |
| 6,068,474 A | 5/2000 | Senn et al. | |
| 6,077,073 A | 6/2000 | Jacob | |
| 6,079,861 A | 6/2000 | Woodward et al. | |
| 6,086,367 A | 7/2000 | Levy | |
| 6,095,812 A | 8/2000 | Senn et al. | |
| 6,099,520 A | 8/2000 | Shimoji | |
| 6,102,696 A | 8/2000 | Osterwalder et al. | |
| 6,123,545 A | 9/2000 | Eggler et al. | |
| 6,132,213 A | 10/2000 | Knorpp et al. | |
| 6,155,823 A | 12/2000 | Nagel | |
| 6,157,661 A | 12/2000 | Walker et al. | |
| 6,159,005 A | 12/2000 | Herold et al. | |
| 6,161,937 A | 12/2000 | Rosenstatter | |
| 6,168,431 B1 | 1/2001 | Narusawa et al. | |
| 6,171,105 B1 | 1/2001 | Sarmadi | |
| 6,186,786 B1 | 2/2001 | Trushkowsky | |
| 6,190,020 B1 | 2/2001 | Hartley | |
| 6,193,510 B1 | 2/2001 | Tsimerman | |
| 6,200,134 B1 | 3/2001 | Kovac et al. | |
| 6,203,325 B1 | 3/2001 | Honkura et al. | |
| 6,208,788 B1 | 3/2001 | Nosov | |
| 6,220,722 B1 | 4/2001 | Begemann | |
| 6,257,883 B1 | 7/2001 | Voudouris | |
| 6,280,187 B1 | 8/2001 | Slone | |
| 6,280,188 B1 | 8/2001 | Ross | |
| 6,282,013 B1 | 8/2001 | Ostler et al. | |
| 6,299,450 B1 | 10/2001 | Honkura et al. | |
| 6,322,358 B1 | 11/2001 | Senn et al. | |
| 6,331,111 B1 | 12/2001 | Cao | |
| 6,345,982 B1 | 2/2002 | Meyer | |
| 6,371,826 B1 | 4/2002 | Pestonji | |
| 6,379,149 B1 | 4/2002 | Franetzki | |
| 6,382,967 B1 | 5/2002 | Rohner et al. | |
| 6,384,099 B1 | 5/2002 | Ostler et al. | |
| 6,419,483 B1 | 7/2002 | Adam et al. | |
| 6,425,761 B1 | 7/2002 | Eibofner | |
| 6,439,888 B1 | 8/2002 | Boutoussov et al. | |
| 6,465,961 B1 | 10/2002 | Cao | |
| 6,468,077 B1 | 10/2002 | Melikechi et al. | |
| 6,482,004 B1 | 11/2002 | Senn | |
| 6,498,108 B2 | 12/2002 | Cao | |
| 6,558,829 B1 | 5/2003 | Faris et al. | |
| 6,561,806 B2 | 5/2003 | Kyotani et al. | |
| 6,634,770 B2 | 10/2003 | Cao | |
| 6,634,771 B2 | 10/2003 | Cao | |
| 6,692,251 B1 | 2/2004 | Logan et al. | |
| 6,692,252 B2 | 2/2004 | Scott | |
| 6,700,158 B1 | 3/2004 | Cao et al. | |
| 6,702,576 B2 | 3/2004 | Fischer et al. | |
| 6,709,128 B2 | 3/2004 | Gordon | |
| 6,709,270 B2 | 3/2004 | Honkura et al. | |
| 6,719,446 B2 | 4/2004 | Cao | |
| 6,719,558 B2 | 4/2004 | Cao | |
| 6,719,559 B2 | 4/2004 | Cao | |
| 6,755,647 B2 | 6/2004 | Melikechi | |
| 6,755,648 B2 | 6/2004 | Cao | |
| 6,755,649 B2 | 6/2004 | Cao | |
| 6,767,109 B2 | 7/2004 | Plank et al. | |
| 6,780,010 B2 | 8/2004 | Cao | |
| 6,783,362 B2 | 8/2004 | Cao | |
| 6,783,810 B2 | 8/2004 | Jin et al. | |
| 6,793,490 B2 | 9/2004 | Bianchetti et al. | |
| 6,799,967 B2 | 10/2004 | Cao | |
| 6,815,241 B2 | 11/2004 | Wang | |
| 6,824,294 B2 | 11/2004 | Cao | |
| 6,829,260 B2 | 12/2004 | Hsia | |
| 6,857,873 B2 | 2/2005 | Bianchetti | |
| 6,890,175 B2 | 5/2005 | Fischer et al. | |
| 6,910,886 B2 | 6/2005 | Cao | |

| | | |
|---|---|---|
| 6,918,762 B2 | 7/2005 | Gill et al. |
| 6,926,524 B2 | 8/2005 | Cao |
| 6,929,472 B2 | 8/2005 | Cao |
| 6,932,600 B2 | 8/2005 | Cao |
| 6,940,659 B2 | 9/2005 | McLean et al. |
| 6,953,340 B2 | 10/2005 | Cao |
| 6,954,270 B2 | 10/2005 | Ostler et al. |
| 6,955,537 B2 | 10/2005 | Cao |
| 6,957,907 B2 | 10/2005 | Fischer |
| 6,969,253 B2 | 11/2005 | Cao |
| 6,971,875 B2 | 12/2005 | Cao |
| 6,971,876 B2 | 12/2005 | Cao |
| 6,974,319 B2 | 12/2005 | Cao |
| 6,979,193 B2 | 12/2005 | Cao |
| 6,979,194 B2 | 12/2005 | Cao |
| 6,981,867 B2 | 1/2006 | Cao |
| 6,981,876 B2 | 1/2006 | Bleckley |
| 6,986,782 B2 | 1/2006 | Chen et al. |
| 6,988,890 B2 | 1/2006 | Cao |
| 6,988,891 B2 | 1/2006 | Cao |
| 6,991,356 B2 | 1/2006 | Tsimerman |
| 6,991,456 B2 | 1/2006 | Plank |
| 6,994,546 B2 | 2/2006 | Fischer |
| 7,001,057 B2 | 2/2006 | Plank |
| 7,011,519 B2 | 3/2006 | Castellini |
| 7,029,277 B2 | 4/2006 | Gofman |
| 7,056,116 B2 | 6/2006 | Scott et al. |
| 7,066,732 B2 | 6/2006 | Cao |
| 7,066,733 B2 | 6/2006 | Logan et al. |
| 7,074,040 B2 | 7/2006 | Kanca |
| 7,077,648 B2 | 7/2006 | Cao |
| 7,086,111 B2 | 8/2006 | Hilscher et al. |
| 7,086,858 B2 | 8/2006 | Cao |
| 7,094,054 B2 | 8/2006 | Cao |
| 7,101,072 B2 | 9/2006 | Takada et al. |
| 7,106,523 B2 | 9/2006 | McLean et al. |
| 7,108,504 B2 | 9/2006 | Cao |
| 7,144,250 B2 | 12/2006 | Fischer et al. |
| 7,153,015 B2 | 12/2006 | Brukilacchio |
| 7,167,824 B2 | 1/2007 | Kallulli |
| 7,172,319 B2 * | 2/2007 | Holder et al. ............ 362/341 |
| 7,182,597 B2 | 2/2007 | Gill et al. |
| 7,189,983 B2 | 3/2007 | Aguirre et al. |
| 7,192,276 B2 | 3/2007 | Fischer et al. |
| 7,202,489 B2 | 4/2007 | Aguirre et al. |
| 7,202,490 B2 | 4/2007 | Aguirre et al. |
| 7,207,694 B1 | 4/2007 | Petrick |
| 7,210,814 B2 | 5/2007 | Scott et al. |
| 7,210,930 B2 | 5/2007 | Kovac et al. |
| 7,223,270 B2 | 5/2007 | Altshuler et al. |
| 7,224,001 B2 | 5/2007 | Cao |
| 7,252,678 B2 | 8/2007 | Ostler et al. |
| 7,267,457 B2 | 9/2007 | Ostler et al. |
| 7,271,420 B2 | 9/2007 | Cao |
| 7,273,369 B2 | 9/2007 | Rosenblood et al. |
| 7,283,230 B2 | 10/2007 | Ostler et al. |
| 7,320,593 B2 | 1/2008 | Ostler et al. |
| 7,323,849 B1 | 1/2008 | Robinett et al. |
| 7,329,887 B2 | 2/2008 | Henson et al. |
| 7,410,282 B2 | 8/2008 | Eichelberger et al. |
| 7,410,283 B2 * | 8/2008 | West et al. ................ 362/573 |
| 7,422,598 B2 | 9/2008 | Altshuler et al. |
| 7,485,116 B2 | 2/2009 | Cao |
| 7,530,707 B2 | 5/2009 | Plank et al. |
| 7,530,808 B2 | 5/2009 | Cao et al. |
| 7,622,467 B2 | 11/2009 | McKinnell et al. |
| 7,651,268 B2 | 1/2010 | Cao et al. |
| 7,654,086 B2 | 2/2010 | Gong et al. |
| 7,661,172 B2 | 2/2010 | Hilscher et al. |
| 7,677,888 B1 | 3/2010 | Halm |
| 7,677,890 B2 | 3/2010 | Turner |
| 7,696,728 B2 | 4/2010 | Cross et al. |
| 7,704,074 B2 | 4/2010 | Jensen |
| 7,712,468 B2 | 5/2010 | Hargadon |
| 7,728,345 B2 | 6/2010 | Cao |
| 7,733,056 B2 | 6/2010 | Hartung et al. |
| 7,758,204 B2 | 7/2010 | Klipstein et al. |
| 7,786,499 B2 | 8/2010 | Cao |
| 2001/0007739 A1 | 7/2001 | Eibofner et al. |
| 2001/0046652 A1 | 11/2001 | Ostler et al. |
| 2002/0014864 A1 | 2/2002 | Gemunder et al. |
| 2002/0051367 A1 | 5/2002 | Hooker et al. |
| 2002/0115037 A1 | 8/2002 | Cao |
| 2002/0133970 A1 | 9/2002 | Gordon et al. |
| 2002/0168603 A1 | 11/2002 | Cao |
| 2002/0168607 A1 | 11/2002 | Cao |
| 2002/0175628 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0190659 A1 | 12/2002 | Cao |
| 2002/0190660 A1 | 12/2002 | Cao |
| 2003/0015667 A1 | 1/2003 | MacDougald et al. |
| 2003/0036031 A1 | 2/2003 | Lieb et al. |
| 2003/0147258 A1 | 8/2003 | Fischer et al. |
| 2003/0148242 A1 | 8/2003 | Fischer et al. |
| 2003/0218880 A1 | 11/2003 | Brukilachchio |
| 2003/0219693 A1 | 11/2003 | Cao |
| 2004/0005524 A1 | 1/2004 | Oxman et al. |
| 2004/0054386 A1 | 3/2004 | Martin et al. |
| 2005/0002975 A1 | 1/2005 | Cao |
| 2005/0077865 A1 | 4/2005 | Durbin et al. |
| 2005/0082989 A1 | 4/2005 | Jones et al. |
| 2005/0093506 A1 | 5/2005 | Hamada et al. |
| 2005/0096661 A1 | 5/2005 | Farrow |
| 2005/0099824 A1 | 5/2005 | Dowling et al. |
| 2005/0116176 A1 | 6/2005 | Acquirre |
| 2005/0142514 A1 | 6/2005 | Scott |
| 2005/0158687 A1 | 7/2005 | Dahm |
| 2005/0171408 A1 | 8/2005 | Parker |
| 2005/0196721 A1 | 9/2005 | Jackson |
| 2006/0024638 A1 | 2/2006 | Rosenblood |
| 2006/0252005 A1 | 11/2006 | Feinbloom et al. |
| 2007/0128577 A1 | 6/2007 | Scott |
| 2007/0228392 A1 | 10/2007 | Plank et al. |
| 2008/0062703 A1 | 3/2008 | Cao |
| 2008/0154249 A1 | 6/2008 | Cao |
| 2008/0161783 A1 | 7/2008 | Cao |
| 2008/0285301 A1 | 11/2008 | Wanninger |
| 2009/0087393 A1 | 4/2009 | Jensen |
| 2009/0092947 A1 | 4/2009 | Cao |
| 2009/0155740 A1 | 6/2009 | Jensen |
| 2009/0227875 A1 | 9/2009 | Cao |
| 2009/0238779 A1 | 9/2009 | Cao |
| 2010/0004640 A1 | 1/2010 | Cao |
| 2010/0096643 A1 | 4/2010 | Cao |
| 2010/0117560 A1 | 5/2010 | Cao |
| 2010/0173267 A1 | 7/2010 | Cao |
| 2010/0207502 A1 | 8/2010 | Cao |

FOREIGN PATENT DOCUMENTS

| | | |
|---|---|---|
| CA | 2298993 | 9/2000 |
| DE | 19624087 | 12/1997 |
| DE | 19803755 | 8/1999 |
| EP | 000266038 | 10/1991 |
| EP | 000568666 | 11/1992 |
| EP | 000320080 | 8/1993 |
| EP | 000591613 | 4/1994 |
| EP | 000672435 | 9/1995 |
| EP | 000678282 | 10/1995 |
| EP | 000709698 | 5/1996 |
| EP | 000755662 | 7/1996 |
| EP | 000736307 | 10/1996 |
| EP | 000750889 | 1/1997 |
| EP | 000780101 | 6/1997 |
| EP | 000780103 | 6/1997 |
| EP | 000830850 | 3/1998 |
| EP | 000879582 | 11/1998 |
| EP | 000880945 | 12/1998 |
| EP | 000884025 | 12/1998 |
| EP | 000885025 | 12/1998 |
| EP | 000959803 | 12/1999 |
| EP | 000998880 | 5/2000 |
| EP | 001031326 | 8/2000 |
| EP | 001090607 | 4/2001 |
| EP | 001090608 | 4/2001 |
| EP | 001093765 | 4/2001 |
| EP | 001103232 | 5/2001 |

| | | |
|---|---|---|
| EP | 001112721 | 7/2001 |
| EP | 001138276 | 10/2001 |
| EP | 001138349 | 10/2001 |
| EP | 000830851 | 5/2002 |
| EP | 000830852 | 5/2002 |
| EP | 001206923 | 5/2002 |
| EP | 01228738 | 8/2002 |
| EP | 001253547 | 10/2002 |
| EP | 000740567 | 11/2002 |
| EP | 001374797 | 1/2004 |
| EP | 1843079 | 10/2007 |
| GB | 002212010 | 7/1989 |
| GB | 002218636 | 11/1989 |
| GB | 002329756 | 3/1999 |
| GB | 002385137 | 8/2003 |
| GR | DE2842938 | 12/1981 |
| GR | DE3411996 | 10/1985 |
| GR | DE3706852 | 8/1988 |
| GR | DE4211233 | 1/1992 |
| GR | DE9017070 | 4/1992 |
| GR | DE2951927 | 2/1997 |
| JP | 0006030275 | 2/1994 |
| JP | 0007240536 | 9/1995 |
| JP | 07240536 | 9/1995 |
| JP | 0008141001 | 6/1996 |
| JP | 08141001 | 6/1996 |
| JP | 0008194786 | 7/1996 |
| JP | 0009010238 | 1/1997 |
| JP | 9010238 | 1/1997 |
| JP | 928719 | 4/1997 |
| JP | 9187825 | 7/1997 |
| JP | 1033573 | 2/1998 |
| JP | 410033573 | 2/1998 |
| JP | 2000312688 | 11/2000 |
| JP | 2001522635 | 11/2001 |
| JP | 2003320683 | 5/2002 |
| JP | 2002200100 | 7/2002 |
| JP | 2003093405 | 4/2003 |
| JP | 200328201 | 10/2003 |
| JP | 2007128667 | 5/2004 |
| JP | 2004355852 | 12/2004 |
| JP | 2005212805 | 8/2005 |
| JP | 2007514454 | 6/2007 |
| WO | WO8301311 | 4/1983 |
| WO | WO8404463 | 11/1984 |
| WO | WO9202275 | 2/1992 |
| WO | WO9309847 | 5/1993 |
| WO | WO9321842 | 11/1993 |
| WO | WO9507731 | 3/1995 |
| WO | WO9519810 | 7/1995 |
| WO | WO9526217 | 10/1995 |
| WO | WO9736552 | 10/1997 |
| WO | WO9737722 | 10/1997 |
| WO | WO9746279 | 12/1997 |
| WO | WO9746280 | 12/1997 |
| WO | WO9803131 | 1/1998 |
| WO | WO9803132 | 1/1998 |
| WO | WO9804317 | 2/1998 |
| WO | WO9909071 | 2/1999 |
| WO | WO9911324 | 3/1999 |
| WO | WO9916136 | 4/1999 |
| WO | WO9920346 | 4/1999 |
| WO | WO9935995 | 7/1999 |
| WO | WO0001464 | 1/2000 |
| WO | WO0002491 | 1/2000 |
| WO | WO0013608 | 3/2000 |
| WO | WO0015296 | 3/2000 |
| WO | WO0041726 | 7/2000 |
| WO | WO0041767 | 7/2000 |
| WO | WO0041768 | 7/2000 |
| WO | WO0043067 | 7/2000 |
| WO | WO0043068 | 7/2000 |
| WO | WO0043069 | 7/2000 |
| WO | WO0045733 | 8/2000 |
| WO | WO0067048 | 11/2000 |
| WO | WO0067660 | 11/2000 |
| WO | WO0103770 | 1/2001 |
| WO | WO0113608 | 2/2001 |
| WO | WO0114012 | 3/2001 |
| WO | WO0119280 | 3/2001 |
| WO | WO0124724 | 4/2001 |
| WO | WO0154770 | 8/2001 |
| WO | WO0160280 | 8/2001 |
| WO | WO0164129 | 9/2001 |
| WO | WO0168035 | 9/2001 |
| WO | WO0169691 | 9/2001 |
| WO | WO0206723 | 1/2002 |
| WO | WO0209610 | 2/2002 |
| WO | WO0211640 | 2/2002 |
| WO | WO0232505 | 4/2002 |
| WO | WO0233312 | 4/2002 |
| WO | WO0249721 | 6/2002 |
| WO | WO02056787 | 7/2002 |
| WO | WO02069839 | 9/2002 |
| WO | WO02080808 | 10/2002 |
| WO | WO2006014363 | 2/2006 |
| WO | WO2009134885 | 11/2009 |

OTHER PUBLICATIONS

Six-page Partial European Search Report for Application No. EP08021597 dated Aug. 27, 2009.

Burgess, John O, et al.; An Evaluation of Four Light-Curing Units Comparing Soft and Hard Curing; Pract. Periodont Anesthet. Dent. 11(1), 125-132, 1999.

Davidson-Kaban, Saliha S., et al.; The Effect of Curing Light Variations on Bulk Curing and Wall-to-Wall Quality of Two Types and Various Shades of Resin Composites; Dent. Mater. 13: 344-352, Nov. 1997.

Feltzer, A.J., et al.; Influence of Light Intensity on Polymerization Shrinkage and Integrity of Restoration-Cavity Interface; Eur. J. Oral Sciences, 103: 322-325, 1995.

Kanca, III, John and Suh, Byoung I.; Pulse Activation: Reducing Resin-Based Composite Contraction Stresses at the Enamel Cavosurface Margins; Am. J. of Dentistry, 12(3), 107-112, 1999.

Kato, Hiromasa; Relationship Between the Velocity of Polymerization and Adaptation to Dentin Cavity Wall of Light-Cured Composite; Dental Materials J. 6(1): 32-37, 1987.

Koran, Peter and Kurschner, Ralf; Effect of Sequential versus Continuous Irradiation of a Light-Cured Resin Composite on Shrinkage, Viscosity, Adhesion, and Degree of Polymerization; Am. J. of Dentistry, 11, No. 1, 17-22, 1998.

LumiLeds Lighting LLC; Luxeon™ Power Light Sources of the Future; Jan. 2001—Mike Holt.

Lumileds Lighting LLC; Application Note 1149-5, Secondary Optics Design Considerations for Super Flux LED's; Copyright © 2000

LumiLeds Lighting, Obsoletes Publication No. 5968-1215E, Publication No. AN06 (Mar. 2000).

Lumileds Lighting LLC; Led Application Note Dental Light Curing; LumiLeds Lighting Publication No. XXX(03.01), Copyright © 2000.

Lumileds Lighting LLC; Concept Evaluation Data Luxeon™ Star 5-Watt; Luxeon™ 5-Watt Preliminary Target Data Sheet, Publication No. JP10 (Jan. 2002).

Lumileds Lighting LLC; Lumen Maintenance of White Luxeon™ Power Light Sources; Application Brief AB07, LumiLeds Lighting, US LLC, Oct. 2001.

Luxeon Dental Technical Data; Power Light Source; Apr. 2002.

Mayes, Joe H., Curing Lights; An Overview, Ormco, vol. 9, No. 2, 2000, p. 15-17.

Mehl, et al.; Softstartpolymerisation von Kompositen in Klasse-V-Kavitatent; Dtsch Zhnarzl Z. 52/1997, pp. 824-827 (in German).

Mehl, et al., Soft Start Polymerization of Composites in Class V Cavities; Dtsch Zhnarzl Z. 52/1997, pp. 824-827 (English version of #15 above.).

Mehl, A., et al., Physical Properties and Gap Formation of Light-Cured Composites With and Without 'Softstart-Polymerization'; J. of Dentistry, 25, 321-330, 1997.

Mehl, et al.; 496 The Influence of Pre-Curing on the Material Properties of Composite Resins; Journal of Dental Research, vol. 74, 1995, Special Issues S.462 (abstract).

Mills, Robin W., et al.; Blue LED's for Curing Polymer-Based Dental Filling Materials; LEO's Newsletter, Jun. 1998.

Mills, R.W., et al.; Optical Power Outputs, Spectra and Dental Composite Depths of Cure, Obtained with Blue Light Emitting Diode (LED and Halogen Light Curing Units LCU's); Oct. 26, 2002.

Reinhardt, et al.; Unischerheiten bei der Prufung von Photopolymerisation; Dtsch zahnarzl Z. 36,635-640, 1981 (in German).

Reinhardt, et al.; Uncertaintaies in the Testing of Photopolymers; Dtsch zahnarzl Z. 36, 635-640 1981 (English Translation).

Sakaguchi, Ronald L. and Berge, Hong Xu; Reduced Light Energy Density Decreases Post-Gel Contraction While Maintaining Degree of Conversion in Composites; J. of Dentistry, 26, 695-700, 1998.

Schlager, Kenneth J., Ignatius, Ronald W.; An LED-Array Light Source for Medical Therapy; SPIE vol. 1892 Medical Lasers and Systems II (1993) p. 26-35.

Swift, Jr., Edward J., et al. Ed.; Contemporary Photocuring Issues, Part II; J. Esthetic Dentistry, 12 (1), 50-57, 2000.

Tarle, Z., et al.; The Effect of the Photopolymerization Method on the Quality of Composite Resin Samples; J. or Oral Rehab. 25: 436-442, 1998.

TIR Technologies, Inc,; Miniaturized TIR lenses for Light Emitting Diodes; TIR Technical Publications, pp. 1-14, Copyright 1992.

Uno, Shigeru and Asmussen, Erik; Marginal Adapation of a Restorative Resin Polymerized at Reduced Rate; Scand J. Dent. Res. 1991; 99: 440-4.

* cited by examiner

CURING LIGHT INSTRUMENT

RELATED APPLICATIONS

This application is a Continuation Application of U.S. patent application Ser. No. 10/215,210 entitled Curing Light Instrument and filed on Aug. 8, 2002, which Application is incorporated herein by reference in its entirety.

FIELD OF THE INVENTION

The present invention relates to light generating instruments for curing light-curable compounds, such as those utilized in dental applications. More particularly, the present invention relates to energy and light efficient curing light instruments.

BACKGROUND OF THE INVENTION

Light-curable compounds, such as adhesives and bonding or filling compounds, are widely used to attach objects to surfaces or to fill gaps or other openings, such as a cavity, in a tooth. Such curable compounds are generally available in a semi-solid state, and are manipulated and positioned on the surface or in the gap as desired, and hardened or cured into a more solid state for permanency. Curing or hardening is generally a chemical polymerization process, which is promoted and driven by various curing conditions and factors. For example, a semi-solid compound or component thereof, may be cured by exposure to air or to energy, such as heat or light energy.

Today, many adhesive and filling compounds are cured by exposure to light energy, particularly visible light energy. The light curing process involves directing a beam of light, such as visible light, at a specific wavelength or band of wavelengths onto a semi-solid light-curable compound to cure the compound. The compound includes light sensitive, chemical components therein which, when exposed to light at the specific wavelength, generally polymerize to harden the compound onto the work surface to bond, fill, or coat the surface.

Specifically, light-curable compounds are widely used in dental procedures. Dentists use light-curable compounds for tooth repairs in a variety of applications including a base, a liner, a coating, a surface seal, a filling for caries and cavities, and to secure crowns or similar dental structures to a tooth surface. Generally, visible light in the blue range of the light spectrum will be sufficient to cure most commonly used dental compounds. Once cured, the dental compound functions, for example, to reduce further tooth decay, to bond dental structures, and/or to provide additional structural support to a tooth.

Generally, curing is effected by various instruments or devices capable of generating visible light, particularly a beam of blue light, and directing this light onto a tooth surface containing the light-curable compound. The blue light penetrates into the compound layer on the tooth surface for complete curing. The duration of the exposure to blue light for proper curing of the compound layer depends upon the light-curable compound itself, thickness of the compound layer, and the power and characteristics of the blue light emitted from the curing light instrument. For example, curing a compound to provide a thin tooth surface coating or veneer will require less light energy, while curing a compound to provide a thicker, deeper filling for gaps, such as caries and cavities, will require a greater amount of light energy.

Presently, the prior art dental curing light devices utilized to deliver blue light to the tooth have exhibited various drawbacks. For example, the blue light directed towards the tooth inevitably exposes the surrounding oral tissue to certain wavelengths of blue light known to be undesirable for human tissue. Hence, curing light devices must be tuned to emit light at the proper wavelength to cure a specific wavelength sensitive light-curable compound for proper curing and have their output radiation limited to within a suitable wavelength band.

Filtering of unwanted wavelengths of light is accomplished by use of complex filtering devices or special filters which receive broad spectrum light from a lamp element, such as a halogen lamp bulb, and allow only the light at the desired blue wavelength to pass through or reflect onto the light-curable compound. The undesired wavelengths are then deflected back into the housing of the instrument adding to the accumulation of heat during operation of the instrument. The heat must be dissipated and therefore, large heat sinks, fans and other devices are necessary. Furthermore, the heat degrades the operation of the bulb and shortens its effective life. In addition, filtering mechanisms often cause a loss of a portion or spectrum of radiation emitted by the light source. Only the specific angle of incidence of light entering the filtering device will be reflected to the curable compound while light outside the specific angle of incidence will be filtered out and lost.

While filtering and angle of incidence effect to decrease light intensity, the light intensity is further diminished by dispersion and scattering of light emitted from the light source. Curing light instruments of the prior art, particularly those utilizing filters, typically have a gap or an empty, hollow space between the light emission source and the filter or other means to direct or transmit the curing light out of the instrument and onto a light-curable compound. However, a portion of the light emitted into this space misses the outlet, thereby reducing the amount of light contacting the light-curable compound.

Thus, curing light instruments of the prior art, with or without filtering devices, are inefficient by virtue of loss of emitted light available to cure the compound. As a result, these instruments require more power output from the light source, increased light emission, and/or longer curing time. Consequently, such instruments also require larger and more efficient heat dissipation components, which increases their overall cost and size. The size, cost of manufacture and operation, and decrease in convenience, to both the operator and the patient, renders these instruments less useful and less desirable.

Thus, there is a need to provide a curing light instrument to cure compounds in a fast, efficient, and effective manner, while improving convenience and reducing size and overall costs.

Accordingly, it is desirable to provide a curing light instrument, which efficiently and effectively cures light-curable compounds by maximizing the amount of light directed onto the light-curable compound.

It is also desirable to provide a curing light instrument, which is small, portable and convenient to use for curing light-curable compounds.

It is further desirable to provide a curing light instrument requiring low maintenance and radiating light from energy efficient light emitting elements having a long life.

SUMMARY OF THE INVENTION

The present invention provides curing light instruments which overcome the weaknesses and drawbacks associated with the prior art light generating instruments by providing an instrument which efficiently and effectively maximizes the light available to cure light-curable compounds. To this end, and in accordance with the principles of the invention, the curing light instrument comprises a housing, a light emitting structure positioned in the housing comprising at least one light emitting die, and a reflector configured to capture and direct light emitted from the die onto a light-curable compound. The reflector is generally a tubular passage having proximal and distal ends, one of which interfaces with the light emitting structure such that a maximum amount of the emitted light is captured and directed onto the light-curable compound.

The housing of the instrument generally includes a handle portion and a barrel portion. The handle portion may house a power source, such as a battery, connected electronically through a control circuit to the light emitting structure. The control circuit controls the time the radiation is emitted, and may further control other factors related to the emission of curing light. The barrel portion of the housing has a proximal end and a distal end. Curing light is radiated directly out of the distal end onto a light-curable compound or alternatively transmitted through a light guide configured to attach to the distal end of the housing. A light shield may be coupled to the distal end of the housing to protect the operator=s eyes from the curing light.

The light emitting structure emits the light necessary to cure the light-curable compound. Light emitting structures, such as structures having at least one light generating die, capable of emitting light, such as blue light, in wavelengths necessary to cure light-curable compounds are suitable. In one embodiment, the instrument utilizes a highly efficient light emitting structure which comprises a collective array of solid state light emitting dies formed on one or more substrates and selectively generates blue light. The first substrate, if only one or the substrate furthest removed from the dies, is generally coupled to an optional base which in turn may be mounted on a printed circuit board. It is beneficial for the printed circuit board, the base, and the substrates to comprise thermally-conductive materials, including metals, such as aluminum, copper and alloys thereof, to conduct heat away from the dies. Cooling of the light emitting structure and corresponding substrates and base may be accomplished by a heat sink thermally coupled to the printed circuit board. Alternatively, a cooling device, such as a fan may be located proximate the heat sink to cool the heat sink and further cool the light emitting structure.

The reflector improves light energy efficiency of the curing light instrument by minimizing or eliminating the loss of light emitted from the light emitting structure thereby maximizing the light radiated out of the instrument housing onto the light-curable compound. To this end, one end of the reflector, such as the proximate end, may be positioned to surround the light emitting structure thereby capturing a significant portion, if not all, of the light emitted and directing this light out of the other end of the reflector. Advantageously, the reflector may comprise a suitable material, such as metal, plastic or glass. To further enhance efficiency, the reflector may have an inner surface comprising a reflective material, such as aluminum or a metal-coated plastic. In one embodiment, the distal end of the reflector is connected to a light guide to transmit the directed light out of the housing.

Accordingly, the present invention minimizes loss, dispersion, and scattering of the light radiation, thereby improving curing efficiency, effectiveness, and decreasing costs associated with curing a light-curable compound on a work surface. The invention is particularly useful for curing light-curable compounds commonly used in dental applications, such as providing an adhesive bond to secure crowns or similar dental structures to a tooth surface, a base, a liner, a coating, or a filling for caries and cavities. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

DETAILED DESCRIPTION OF THE INVENTION

The present invention provides curing light instruments to cure light-curable compounds, such as dental compounds, efficiently and effectively from a cost and energy perspective. While the invention will be described in one embodiment herein as having application to curing dental compounds, it is not so specifically limited. Also, the curing light instrument illustrated herein is portable, however, the invention is not so limited and could alternatively be plugged into a source of power. Portability, of course, provides added convenience of use.

Figure 1:
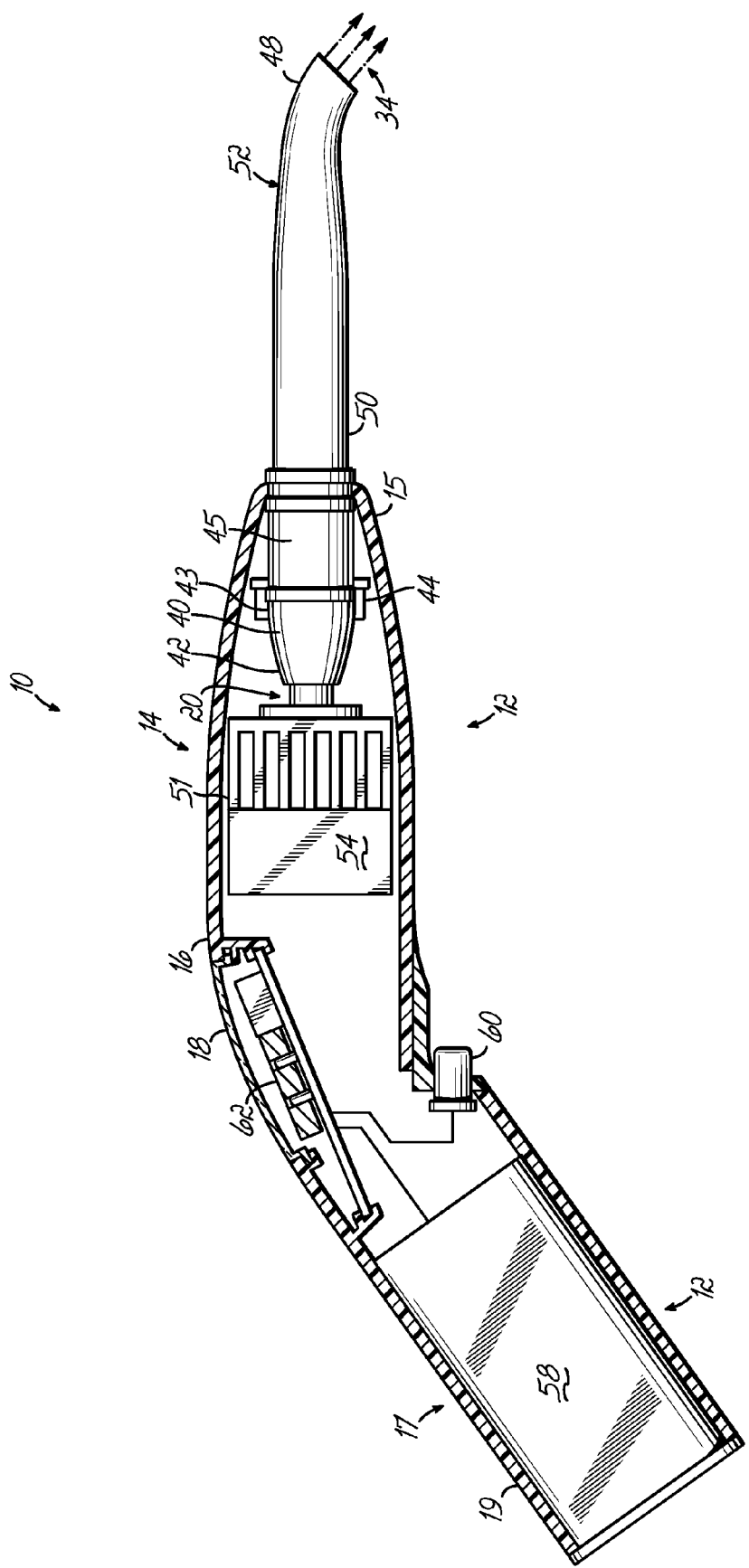
FIG. 1 is an internal view of the housing of one embodiment of a curing light instrument.

FIG. 1 illustrates one embodiment of the curing light instrument. As shown, the curing light instrument 10 comprises a housing 12, a light emitting structure 20 positioned within the housing 12, and a reflective element or reflector 40 configured to interface with the light emitting structure 20, such that reflector 40 captures light emitted from the light emitting structure 20 and directs it onto a light-curable compound to cure the compound.

As shown in FIG. 1, housing 12 of instrument 10 is generally a gun-shaped structure having a barrel portion 14 coupled to a handle portion 17. Barrel portion 14 of housing 12 generally includes a distal end 15 and a proximal end 16. Handle portion 17 of housing 12 generally includes a distal end 18 and a proximal end 19. Proximal end 16 of the barrel portion 14 is generally a continuation in structure of the distal end 18 of the handle portion 17. While references are made to the ends of portions 14, 17, for illustration, the housing is not limited to such references. Advantageously, the barrel portion 14 will house the light emitting structure 20. The housing 12, including the barrel portion 14 and the handle portion 17, may be composed of any suitable materials, such as those typically used in the art. Particularly useful are lightweight compact flame resistant materials, such as plastic. In addition, either or both of the barrel portion 14 and handle portion 17 of the housing 12 may be vented for purposes of dissipating heat generated by light emitting structure 20. It is particularly beneficial to vent that portion which houses the light emitting structure 20.

Figure 3:
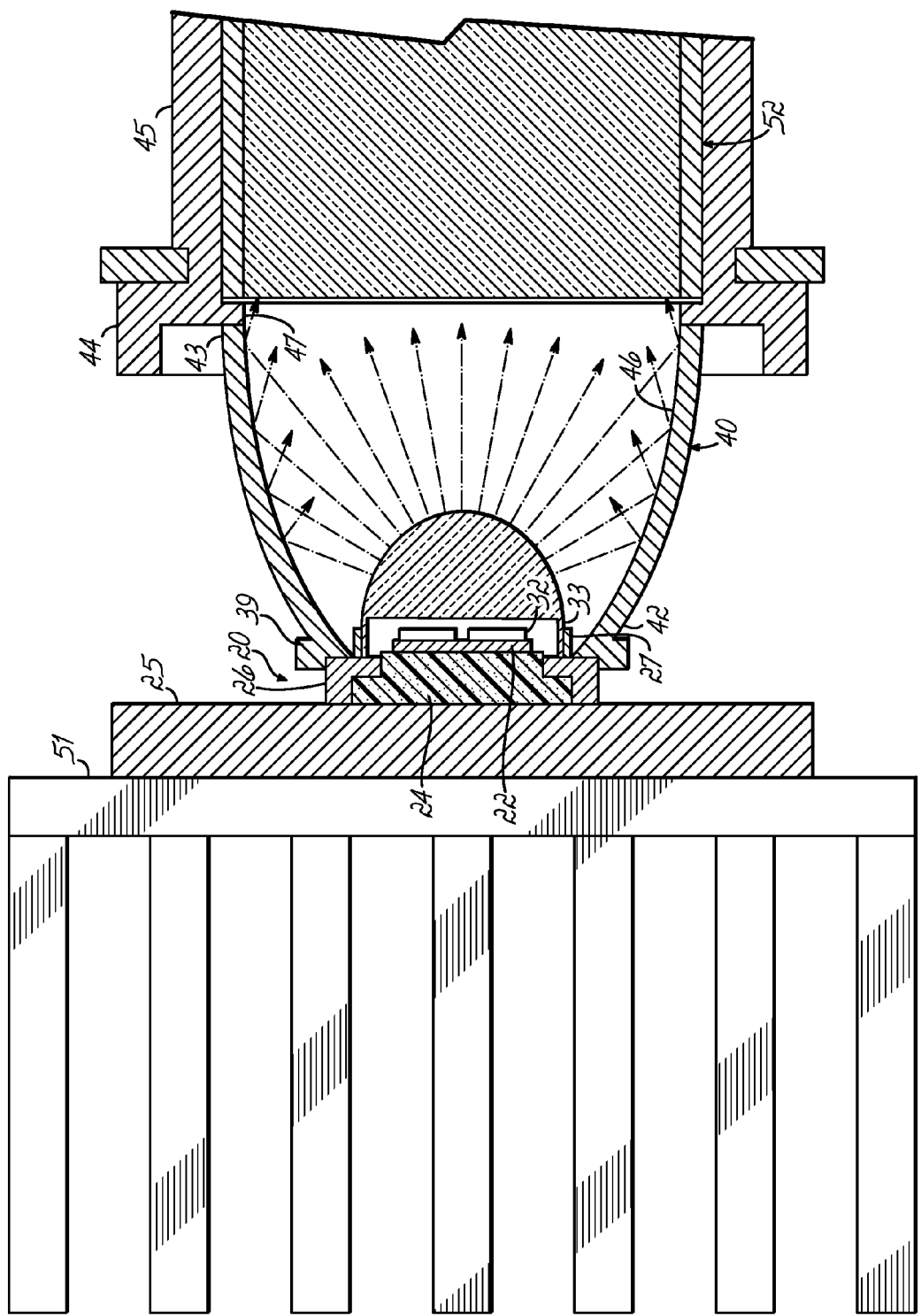
FIG. 3 is a magnified cross-sectional view of the reflector-light emitting structure interface illustrated in FIG. 2.
Figure 4:
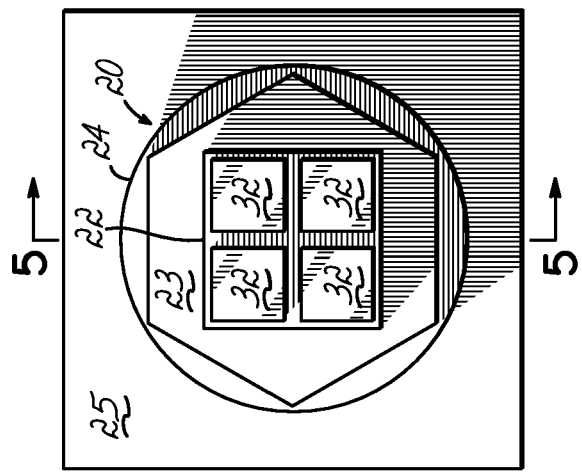
FIG. 4 is an overhead view of one embodiment of a light emitting structure.

Light emitting structure 20 is capable of emitting light 34 having wavelengths suitable to cure a light-curable compound. Advantageously, the light emitting structure 20 emits a narrow wavelength band of radiation or light sufficient to cure the compound. Referring to FIGS. 3 and 4, the light emitting structure 20 comprises at least one light emitting element or die 32. Die 32 generates light 34 for transmission out of the distal end 15 of barrel portion 14 of the housing 12 onto a light-curable compound (not shown). As shown in FIG. 3, light 34 is not directed, rather it is generally emitted in various directions. In the exemplary embodiment disclosed herein, each die 32 is generally made of light generating semiconducting material. The dies 32 are not individually packaged with individual reflectors and individual lenses. Rather, the dies 32 are unpackaged junctions which, when electrically biased, generate light in a desirable narrow band of wavelengths. Each die 32 typically requires approximately 4-5 volts of DC bias. In the disclosed embodiment, the die 32 is appropriately biased for operation. Die 32 may generally be any shape, such as a square as shown in FIG. 4. Die 32 may be of suitable size, advantageously small enough to provide a compact instrument 10. In one embodiment, the die 32 is in the order of 1.0 mm on a side or 1.0 mm$^2$ in area.

FIG. 4 illustrates one embodiment of a light emitting structure 20 suitable for the invention. As shown, light emitting structure 20 may comprise an array of four dies 32 which, at a suitable power level, collectively provide a very high density of light to effectively cure a light-curable compound. By virtue of its small size, die 32 provides a collective array which overall requires much less surface area than conventionally packaged LEDs, such as those used in the prior art. Each die 32 may be arranged or spaced as desired to form the array. It is important to keep the density of the light 34 to a maximum. Thus, the dies 32 are laid out to avoid any blank spots in the generated light pattern. In accordance with the embodiment illustrated in FIG. 4, dies 32 are formed side-by-side in a matrix resembling a square to supply a continuous pattern of light. The matrix or array arrangement may be any shape, and advantageously, one corresponding to the shape of the underlying substrate layer 22. Other factors influencing the size and shape of the array include light requirements for the instrument, the cooling system available, and the light output of the available die. In addition, the number of dies 32 may increase or decrease depending upon the type of compound to be cured and the types of dental applications for which the instrument 10 is used. For example, curing a deep filling or thicker surface coating may require stronger radiation which may be provided by more than four dies 32. Further, different light amounts and intensities may be necessary depending upon the sensitivity of the compound. Accordingly, the present invention is not limited by the number of dies utilized.

A suitable light emitting structure 20 may further comprise a first substrate, a base, and optionally a second substrate, positioned between the first substrate on which the dies are formed and the base. The light emitting structure 20 may further comprise a printed circuit board on which the first substrate, second substrate, or base is mounted. Referring to FIG. 3, the first substrate 22, a surface on which the collective array of dies 32 are formed, advantageously provides a means to cool the light emitting structure 20. To this end, substrate 22 may comprise thermally-conductive materials to dissipate the heat generated by the dies 32. For example, the substrate 22 may be formed of a ceramic material, such as alumina or silica. In other embodiments, there may be more than one substrate. For example, as shown in embodiments illustrated in FIGS. 4 and 5, light emitting structure 20 has a first substrate 22 and a second substrate 23. The shapes of each substrate may vary and may depend upon the design and space available in instrument 10, and number of dies 32. For example, as illustrated in FIG. 4, the first substrate 22 may be square in shape and the second substrate 23, coupled to the first substrate 22 on a surface opposing the dies 32, may be hexagonal in shape. For efficient cooling purposes, it is beneficial to have each subsequent substrate subsequently removed from the dies 32 to be successively larger in size. Thermally coupling the finally removed substrate to a base 24 is beneficial for further support and added cooling.

Figure 5:
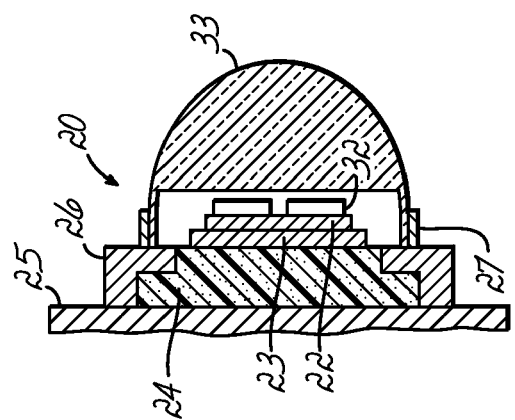
FIG. 5 is a cross-sectional view of the light emitting structure shown in FIG. 4, enclosed by a lens.

FIG. 5 illustrates the embodiment of the light emitting structure 20 illustrated in FIG. 4 viewed from a cross-sectional perspective and enclosed by a lens. As shown, the light emitting structure 20 includes a base 24 positioned between the second substrate 23 and the printed circuit board 25. The base 24 generally comprises one or more thermally-conductive materials, including aluminum, copper, gold, silver and silicon. Base layer 24 is advantageously an aluminum slug. The base 24 may in turn be mounted on the printed circuit board 25 by conventional techniques, such as by the use of bolts or other fasteners, or alternatively without fasteners, such as with thermal cement or other securing members. As illustrated, the base 24 is mounted or secured to the printed circuit board 25 by a plastic housing 26 configured to accomplish such attachment. In addition to plastic housing 26, the secured base 24 is further mounted by use of a cement (not shown).

Figure 2:
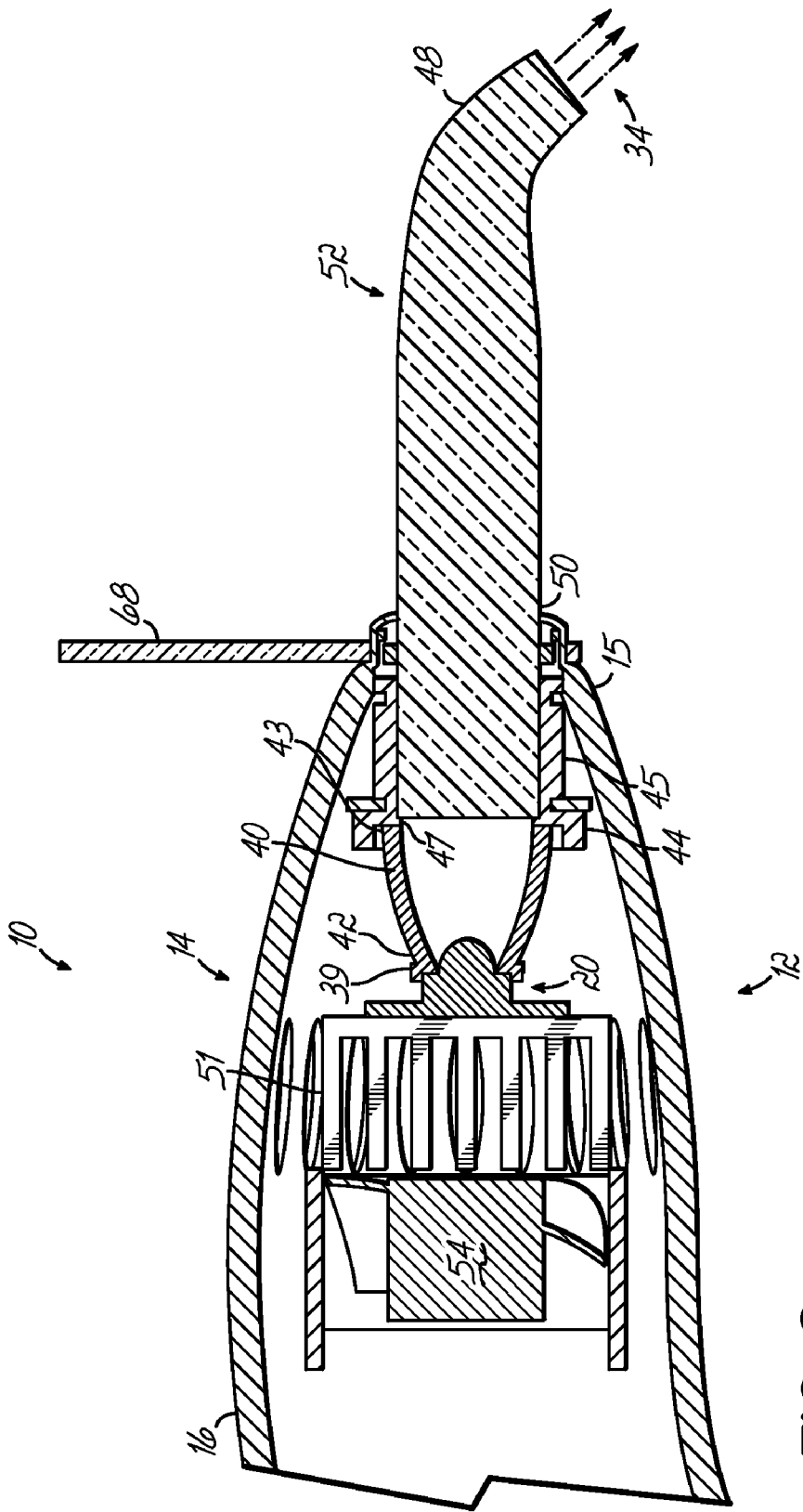
FIG. 2 is a cross-sectional view of the barrel portion of the housing illustrated in FIG. 1.

Printed circuit board 25 generally serves to relay the necessary electrical energy, generally through electrical leads, to the dies 32 to generate light. Printed circuit board 25 may additionally provide cooling for the light emitting structure 20. Accordingly, printed circuit board 25 may comprise thermally conductive materials including metals, such as aluminum, copper, silicon and alloys thereof. Advantageously, the printed circuit board 25 will comprise aluminum, thus maximizing the dissipation of heat emitted by dies 32 during the operation. The printed circuit board 25, and therefore the light emitting structure 20, may be supported by the housing via direct attachment or indirect attachment through an intermediary structure, such as a heat sink 51 (FIG. 3). Heat sink 51 provides additional cooling for the instrument 10. Further cooling may be accomplished with a forced air element, such as a fan 54 (FIG. 2), used to direct or force air over the heat sink 51 and/or the light emitting structure 20. As shown in FIG. 2, fan 54 may be thermally coupled to heat sink 51.

The light emitting structure 20 depicted in the figures provides many advantages over those used in prior art instruments. Some of the advantages include extremely high flux and flux density, and a longer operating life in the range of up to 10,000 hours for the light-generating components. The die 32 are solid state devices having significantly long life spans as compared to prior art bulbs. This translates into cost savings and convenience for the operator by providing a curing light instrument 10 having a longer useful lifetime without the need to constantly replace bulbs.

A particularly important advantage is that light emitting structure 20 allows instrument 10 to emit desired light, such as blue light radiation, necessary to cure specific compounds. In one embodiment, the die 32 provides radiation in a blue light at a desirable band of wavelengths, for example, around 470 nanometers. Such blue light is useful for curing dental compounds, particularly those being currently used in tooth repairs. To this end, the present invention eliminates the need for filtering devices, typically used to filter undesired wavelengths of broad spectrum light, as is required with prior art halogen lamp bulbs. In addition, the light emitting structure 20 is generally more energy efficient than incandescent and most halogen lamps. Furthermore, the emitted light tends to be cooler, safer to touch, and generally turns on/off instantaneously. One embodiment of a light emitting structure 20 suitable for the present invention is available from Lumileds Lighting Company, U.S.

In accordance with the principles of the invention, the light radiated from the light emitting structure 20 is efficiently captured and directed for effective curing. As mentioned before, the dies 32 emit light 34 which is scattered and multi-directional and not in the form of a dense beam directed in any particular direction. As shown in FIGS. 2 and 3, the light emitting structure 20 is interfaced with a reflector 40 such that a light 34 generated by the light emitting structure 20 is emitted into the reflector 40 despite the multi-directional emission. Advantageously, reflector 40 is configured to surround the light emitting structure 20. This surrounding relationship between the reflector 40 and the light emitting structure 20 may structurally be any interfacing relationship provided that the configuration ensures that a substantial portion of light 34 is captured by reflector 40. For example, as illustrated in FIG. 2, reflector 40 may be configured to enclose dies 32 and any or all substrates 22 and/or 23, and interface with the base 24 (if present). Alternatively, reflector 40 may interface with support members 26 securing base 24 to the printed circuit board 25 (FIG. 3). Accordingly, reflector 40 allows the curing light instrument 10 to be efficient from an energy and light perspective by minimizing a loss of light 34 radiated from light emitting structure 20. To this end, reflector 40 also minimizes the loss of curing ability due to scattering and dispersion of the light, as seen with the instruments of the prior art. Further, reflector 40 reduces the power requirements for the light emitting structure 20 thereby reducing the cooling requirements of curing light instrument 10.

Figure 6:
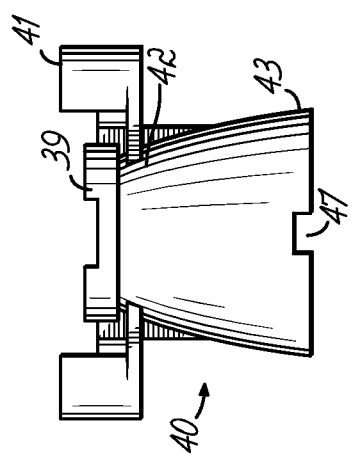
FIG. 6 is a side view of a reflector.

Reflector 40, in the exemplary embodiment illustrated in FIG. 6, is generally a tubular shaped structure having a proximal end 42 and a distal end 43. Referring to FIG. 3, the proximal end 42 surrounds the light emitting structure 20 so that light 34 is emitted directly into the reflector 40. The specific sizes and dimensions, such as the diameter and length, of the reflector 40 may vary and will generally depend upon the size of the interfacing component of the light emitting structure 20. In the embodiment shown in FIG. 6, the proximal and distal ends, 42 and 43 respectively, of reflector 40 have different dimensions. The shape of distal end 43 of reflector 40 may vary depending upon the ability to interface with other desired structural elements of instrument 10, such as a light guide 52.

Figure 7:
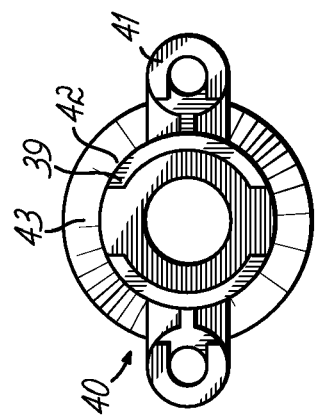
FIG. 7 is a bottom view of the reflector illustrated in FIG. 6.

Reflector 40 may generally be supported by housing 12, advantageously at distal end 15 of barrel portion 14 of housing 12. Alternatively, reflector 40 may be supported through attachment to another structural component of instrument 10. For example, reflector 40 may be supported via attachment to light emitting structure 20. More particularly, as illustrated in FIGS. 6 and 7, reflector 40 may integrally include a support member 39 to secure reflector 40 to light emitting structure 20 and/or a support member 41, which can secure reflector 40 to base 24 or to printed circuit board 25. Alternatively, as shown in FIGS. 2 and 3, the reflector 40 may be supported by coupling to an adapter 45. As shown in FIGS. 3 and 6, reflector 40 may have a locating notch or groove 47, which may be intimately adapted to receive a finger on adapter 45 so as to prevent movement and decoupling of reflector 40 from a light guide 52. Any means of support for the reflector 40 provides additional support for the light emitting structure 20. Reflector 40 improves the curing efficiency of instrument 10. To this end, reflector 40 may be formed of a suitable material which is capable of reflecting light. The reflector 40 may be made of a suitable material, such as plastic, glass, or a metal. Plastic is a lightweight material, allowing instrument 10 to be inexpensively fabricated. For materials like plastic which do not inherently reflect light, the reflector 40 may advantageously have a reflective coating on an inner surface 46 (FIG. 3). Inner surface 46 captures the light emitted in from die 32 and directs it onto the light-curable compound. Accordingly, surface 46 generally comprises a reflective material, including metals such as aluminum. Advantageously, surface 46 will be aluminum. Referring to FIG. 2, the reflector 40 directs the light 34 to other structural components, such as a light guide 52, or out of the housing 12. The combination of the reflector 40 and the array of dies 32 maximizes the amount of light 34 provided for curing.

Adapter 45 not only serves to secure or support reflector 40, but also to couple reflector 40 to a light guide 52. More specifically, adapter 45 is configured to couple to the distal end 43 of the reflector 40 and to the proximal end 50 of the light guide 52. In this manner, the adapter 45 couples the reflector 40 to the light guide 52 so as to provide one continuous interface without a loss of light. Adapter 45 may be formed of a lightweight material, such as plastic.

The embodiment of the instrument 10 illustrated in FIG. 1 includes a light guide 52 configured to interface with the reflector 40 and to receive and transmit the light 34 directed therefrom. The light guide 52 generally comprises a distal end 48 and a proximal end 50. As shown in FIG. 1, the light 34 is received by the proximal end 50 of light guide 52, also referred to as the receiving end, and transmitted out of the distal end 48 of light guide 52, also referred to as the transmission end. Proximal end 50 is generally removably secured to the housing 12, or to the reflector 40 or adaptor 45. Conventional securing means are suitable. For example, proximal end 50 may be snapped into and out of the distal end 15 of housing 12 or into and out of the distal end 43 of the reflector 40 or adaptor 45.

Light guide 52 may generally be any shape effective to transmit light. Preferably, the shape of the light guide 52 will be adapted for convenience of use depending upon the work surface. For instance, while the light guide 52 may have a relatively uniform diameter from the proximal end 50 through the distal end 48, advantageously, distal end 48 will have a smaller diameter then proximal end 50 to increase the intensity of the exiting light 34 and improve the curing efficiency and convenience of use of the instrument 10. In one embodiment of the invention the reflector 40 is configured to fill a conventional 13 mm light guide. The adaptor 45 is also configured to interface with a 13 mm light guide. While suitable light guides 52 may be commercially available in a variety of different sizes and shapes, for example, in diameters of 8 mm, 11 mm, and 13 mm, respectively, it has been discovered that a distal end 48 diameter of about 11 mm will allow sufficient exposure of the light-curable compound to light 34 and curing of the compound without significant movement of distal end 48 around the work surface. In one embodiment of the invention, a light-receiving end 50 at 13 mm is tapered down to a light-output end of around 11 mm. The larger proximal end 50 of about 13 mm allows the light guide 52 to maximize the capture of light 34 from the reflector 40 thereby further improving the light curing efficiency of instrument 10. The 11 mm distal end concentrates the light 34 to allow a higher intensity of light than a conventional 11 mm or 13 mm light guide. Therefore, in the one embodiment, light guide 52 has a proximal end or receiving end 50 having a diameter of about 13 mm and a distal end or transmitting end 48 having a smaller diameter of about 11 mm. Furthermore, slight bending or tapering of the light guide 52 between the distal end 48 and the proximal end 50 allows the user to cure compounds on work surfaces which would otherwise be difficult to reach. As shown in FIG. 1, light guide 52 is advantageously tapered proximate the distal end 48.

Generally, the light guide 52 will comprise components capable of effectively transmitting light 34. For example, one embodiment of the invention utilizes a light guide 52 comprising a plurality of optical fibers (not shown) which are operably fused together into a single light guide or light pipe type structure to transmit the light 34. In another embodiment, the light guide 52 utilizes a plurality of individual optical fibers or strands which collectively form a conductor. Each strand in the conductor has a taper separate from the taper of each other strand. For example, to form a conductor having individual tapered strands, each of the fiber-optic strands may be separately tapered, bundled and fused together to form a solid conductor. The solid conductor may then be stretched to form an elongated stretch section of conical geometry wherein each strand is uniformly tapered over the stretched section. The combined bundle of tapered strands generally imparts a taper to the light guide 52. This solid conductor generally has a light receiving end or proximal end 50 and a light transmitting end or distal end 48 as described above. Further details and additional light guides 52 which are suitable for the present invention are set forth in the U.S. Pat. No. 5,371,826, titled "Dental Fiber-optic Light Bundle with Uniform Taper" and herein incorporated by reference in its entirety. Also, conventional light guides known in the art are suitable for the invention.

A shield 68 (FIG. 2) may be attached to instrument 10 to protect the operator (not shown) from exposure to light reflected during curing operations. Shield 68 may generally be configured to be easily secured or removably secured to the light guide 52, beneficially to the receiving end 50 of light guide 52. Alternatively, in an embodiment of the instrument 10 where a light guide 52 is not included, shield 68 may be secured to the distal end 15 of barrel portion 14 of housing 12.

FIG. 5 illustrates one embodiment of the inventive instrument 10 wherein the light emitting structure 20 is generally encapsulated by a lens 33. Lens 33 is placed over a collective array of dies 32 and directs the light 34 generated therefrom. Lens 33, therefore, may beneficially comprise an optically refractive material placed as a continuous layer over the dies 32. For example, lens 33 may be made of clear plastic. Lens 33 may be supported or held in place by conventional means, such as, but not limited to, one or more support legs 27. Legs 27 may be configured to attach to plastic housing 26 of light emitting structure 20. Lens 33 is surrounded by reflector 40 such that the light 34 is refracted, without escape, into the reflector 40. To this end, lens 33 eliminates the need for a larger focusing lens having drawbacks discussed earlier.

Referring again to FIG. 1, the curing light instrument 10 may also comprise a power source, such as a power supply, to power the curing light instrument 10 and particularly, the light emitting structure 20. The power supply may be a portable power supply, such as a battery 58, contained in the housing 12. Advantageously, battery 58 will be a rechargeable battery contained in the handle portion 15 of housing 12. Alternatively, the curing light instrument 10 may be powered by an external source such as an AC power source coupled to a converter to supply DC power to the light emitting structure 20. Persons of ordinary skill in the art will readily understand that such an external source may be supplied through an electrical cord (not shown) to the curing light instrument 10. The power supply is typically coupled to a control circuit 62 which allows control, regulation, or conditioning of the power or electrical energy supplied to the light emitting structure 20.

The embodiment illustrated in FIG. 1 is an instrument 10 allowing the operator to control the timing requirements of light 34 emitted. As shown, a trigger switch 60, which may be located in the handle portion 17 of the housing 12, is generally used to power the light emitting structure 20. Trigger switch 60 is electrically coupled to the control circuit 62 and controls the ON/OFF function of light 34 emitted from the light emitting structure 20. Further switches (not shown) may also be located in the housing 12, for example in the handle portion 17, to control other aspects of the emission of curing light 34. For instance, instrument 10 may have a second switch (not shown) designed to control the power flowing to the light emitting structure 20 and/or to regulate the level or power of the radiation emitted. In such an instrument, these control switches would also be coupled to control circuit 62 to allow the operator complete control over all aspects necessary to properly cure the compound. Control circuit 62 may generally be positioned and supported by the housing 12. As shown in FIG. 1, the control circuit may be located in the distal end 18 of handle portion 17 of housing 12.

The present invention also provides a method to cure light-curable compounds. While the method refers to curing compounds used in dental applications, the invention is not so limited. Generally, the operator, a dentist for example, initially positions the curing light instrument in proximity to the compound. The operator grips the instrument 10 at the handle portion 17 of housing 12 and directs the light transmitting end, typically the distal end 15 of barrel portion 14, towards the work surface (not shown), such as a tooth. The operator then activates the curing light instrument 10 by adjusting and/or depressing the trigger switch 60 appropriately to generate light, or turn ON light 34, to begin to cure a light-curable compound. The light emitting structure 20 then emits light 34 having the desired power and wavelength to cure the compound. In one embodiment, the light emitted will have a power in the range of from about 200 to about 1400 mW/cm$^2$. The multi-directional light 34 emitted is captured and directed by the reflector 40 onto a light-curable compound to cure the compound. Once the operator is satisfied that the compound has been cured, the curing light may be turned OFF by simple release of the trigger switch 60. Where the curing light instrument includes a light guide 52, the operator positions the transmission end 48 of the light guide 52 into the mouth of a patient in proximity to the compound and radiates the light 34 to effect the dental repair.

Thus, the invention provides a small, compact, durable, and portable curing light instrument for hardening or curing light-curable materials used in dental applications. The invention also eliminates the need for filters by providing a light emitting structure comprising dies which generate a desired narrow wavelength band of blue light. Also, the dies have long useful lifetimes and state of the art light generating capabilities. In addition, the invention includes an appropriately dimensioned reflector, strategically interfaced with the light emitting structure, to reduce or eliminate the loss of light radiation emitted thereby reducing both the required periods of light emission and power requirements of the instrument as a whole. To this end, the inventive instrument reduces the heat generated within the instrument housing and eliminates the need for complicated cooling systems. Thus, the inventive instrument is efficient with respect to curing times and heat generation. In addition, the small size of the highly efficient light emitting structure provides an instrument which may be assembled in a housing generally smaller than instruments of the prior art. To this end, the device is lighter and easier for the operator to manipulate. Also, the portable nature of the device allows the operator to carry the instrument and use as needed.

While the present invention has been illustrated by a description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details and representative apparatus and method, and illustrative examples shown and described. Accordingly, departures may be made from such details without departing from the spirit or scope of the applicant=s general inventive concept.

What is claimed is:

1. An instrument for curing light-curable compounds comprising:
   a housing;
   a light emitting structure positioned in the housing and including at least one light emitting die mounted on a substrate;
   a lens structure positioned proximate to the die and positioned over the die and at least a portion of the substrate to capture light from the die, the lens structure extending forwardly of the die to refract captured light;
   a reflector configured for being positioned with the light emitting structure and configured to capture light emitted from the die, the reflector being a tubular structure having open proximal and distal ends;
   the lens structure and die being positioned proximate to the open proximal end of the reflector and the lens structure extending into the tubular reflector structure from the proximal end so the light is refracted into the reflector and directed toward the distal end and onto a light-curable compound;
   a light guide operably coupled to the distal end of the reflector, the light guide including a plurality of fiber-optic strands capable of transmitting light along the length of the light guide for transmitting light captured by the reflector onto a light-curable compound.

2. The instrument of claim 1 wherein the light emitting structure comprises a plurality of dies to form an array.

3. The instrument of claim 1 wherein the first substrate comprises a thermally conductive material.

4. The instrument of claim 1 wherein the reflector is configured of at least one of a plastic, metal and glass.

5. The instrument of claim 1 further comprising a heat sink thermally coupled to the light emitting structure to absorb heat generated therefrom.

6. The instrument of claim 1 further comprising a light shield removably mounted to the housing to prevent reflection of curing light to an operator during use of the instrument.

7. The instrument of claim 1 further comprising a fan positioned in the housing to cool the light emitting structure.

8. The instrument of claim 1 further comprising a portable power supply positioned within the housing for providing power to the light emitting structure.

9. The instrument of claim 1 further comprising a base coupled to the first substrate, the base comprising a thermally conductive material.

10. The instrument of claim 1 wherein said housing comprises a barrel portion, and a handle portion coupled to the barrel portion, wherein an end of the barrel portion is configured to support a light guide for transmitting light out of the barrel portion of the housing and to the light-curable compound.

11. The instrument of claim 1 wherein the fiber-optic strands are bundled together to form a solid conductor, the strands being individually tapered to impart a taper to the light guide.

12. The instrument of claim 11 wherein the solid conductor comprises a light receiving end and a light transmitting end, the light receiving end having a diameter of about 13 mm and the light transmitting end having a diameter of about 11 mm.

13. The instrument of claim 11 wherein the fiber-optic strands are tapered at an angle less than one-tenth of a degree (<0.1°), and the taper angle for said light guide is less than five degrees (5°).

14. The instrument of claim 9 wherein the thermally conductive material is at least one of aluminum, copper, gold, and silver.

15. The instrument of claim 9 further comprising a second substrate positioned between the base and the first substrate.

16. The instrument of claim 15 wherein the second substrate comprises a thermally conductive material.

17. The instrument of claim 1 further comprising a printed circuit board coupled to the first substrate.

18. The instrument of claim 9 further comprising a printed circuit board coupled to the base.

19. The instrument of claim 18 wherein the printed circuit board comprises aluminum.

20. An instrument for curing light-curable compounds comprising:
    a housing;
    a light emitting structure comprising a plurality of solid state light emitting dies forming a collective array on a first substrate;
    a lens structure positioned proximate to the array and positioned over the array of dies to capture light collectively from the dies, the lens structure extending forwardly of the array to refract captured light;
    a reflector forming a generally tubular passage having open proximal and distal ends, the lens structure and array being positioned proximate the open proximal end and the reflector configured to surround the array of dies with the lens structure extending through the proximal end, the reflector operable to capture and direct light emitted by the array of dies toward the distal end;
    a light guide operably coupled to the distal end of the reflector, the light guide including a plurality of fiber-optic strands capable of transmitting light along the length of the light guide for transmitting light captured by the reflector onto a light-curable compound.

21. The instrument of claim 20 wherein the reflector is configured of at least one of a plastic, metal and glass.

22. The instrument of claim 20 wherein the reflector couples proximate the light emitting structure to surround the dies and capture light emitted therefrom.

23. The instrument of claim 20 wherein the fiber-optic strands are bundled together to form a solid conductor, the strands being individually tapered to impart a taper to the light guide.

24. The instrument of claim 23 wherein the solid conductor comprises a light receiving end and a light transmitting end, the light receiving end having a diameter of about 13 mm and the light transmitting end having a diameter of about 11 mm.

25. The instrument of claim 23 wherein the fiber-optic strands are tapered at an angle less than one-tenth of a degree (<0.1°), and the taper angle for said light guide is less than five degrees (5°).

26. The instrument of claim 20 further comprising a printed circuit board formed of a thermally conductive material, the printed circuit board coupled to the first substrate on a side opposing the collective array of dies.

27. The instrument of claim 26 wherein the printed circuit board is formed of aluminum.

28. The instrument of claim 26 further comprising a heat sink thermally coupled to the printed circuit board.

29. The instrument of claim 28 further comprising a forced air device for directing air proximate the heat sink.

30. The instrument of claim 20 further comprising a portable power supply positioned within the housing to provide power to the light emitting structure.

31. The instrument of claim 26 further comprising a second substrate formed of a thermally conductive material positioned between the printed circuit board and the first substrate.

32. The instrument of claim 26 further comprising a base formed of a thermally conductive material positioned between the printed circuit board and the first substrate.

33. The instrument of claim 20 further comprising an adaptor, the adaptor configured to interface with the distal end of the reflector and an end of the light guide for coupling the light guide and reflector.

34. The instrument of claim 32 wherein the base is formed of one of aluminum, copper, gold and silver.

* * * * *